(12) United States Patent
Kruger et al.

(10) Patent No.: US 9,097,625 B2
(45) Date of Patent: Aug. 4, 2015

(54) GAS INJECTION SYSTEM FOR ENERGETIC-BEAM INSTRUMENTS

(71) Applicant: Omniprobe, Inc., Dallas, TX (US)

(72) Inventors: Rocky Kruger, Dallas, TX (US); Aaron Smith, Dallas, TX (US); Cheryl Hartfield, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 13/864,362

(22) Filed: Apr. 17, 2013

(65) Prior Publication Data

US 2014/0014742 A1    Jan. 16, 2014

Related U.S. Application Data

(60) Provisional application No. 61/671,473, filed on Jul. 13, 2012.

(51) Int. Cl.

| | | |
|---|---|---|
| *C23C 16/00* | (2006.01) | |
| *G01N 1/28* | (2006.01) | |
| *C23C 16/448* | (2006.01) | |
| *C23C 16/48* | (2006.01) | |
| *C23C 16/52* | (2006.01) | |
| *C23C 16/56* | (2006.01) | |
| *H01J 37/02* | (2006.01) | |

(52) U.S. Cl.
CPC ............... *G01N 1/28* (2013.01); *C23C 16/448* (2013.01); *C23C 16/48* (2013.01); *C23C 16/52* (2013.01); *C23C 16/56* (2013.01); *H01J 37/02* (2013.01); *H01J 2237/006* (2013.01); *H01J 2237/317* (2013.01)

(58) Field of Classification Search
USPC .............................................. 118/723 FI, 726
See application file for complete search history.

(56) References Cited

U.S. PATENT DOCUMENTS

| | | | |
|---|---|---|---|
| 3,847,115 A | 11/1974 | Tashbar | |
| 4,058,120 A | 11/1977 | Caparrelli et al. | |
| 4,506,815 A * | 3/1985 | Melas et al. .................. | 222/630 |
| 4,813,373 A * | 3/1989 | Demay et al. ................ | 118/726 |
| 5,120,925 A | 6/1992 | Ohnishi et al. | |
| 5,182,170 A | 1/1993 | Marcus et al. | |

(Continued)

FOREIGN PATENT DOCUMENTS

JP            11086772 B2     3/1999

OTHER PUBLICATIONS

International Searching Authority, International Application No. PCT/US2013/036554, International Search Report and the Written Opinion, Sep. 25, 2013.

(Continued)

*Primary Examiner* — Keath Chen
(74) *Attorney, Agent, or Firm* — John A. Thomas

(57) ABSTRACT

A gas injection system for an energetic-beam instrument having a vacuum chamber. The system has a cartridge containing a chemical serving as a source for an output gas to be delivered into the vacuum chamber. The cartridge has a reservoir containing the chemical, which rises to a fill line having a level defined by an amount of the chemical present in the reservoir at a given time. An outlet from the reservoir is coupled to an output passage through an outlet valve and configured so that when the system is tilted the outlet remains above the level of the fill line. Embodiments include isolation valves allowing the cartridge to be disconnected without destroying system vacuum.

20 Claims, 15 Drawing Sheets

(56) References Cited

U.S. PATENT DOCUMENTS

| | | | |
|---|---|---|---|
| 5,288,367 A | 2/1994 | Angell et al. | |
| 5,683,547 A | 11/1997 | Azuma et al. | |
| 6,118,122 A | 9/2000 | Koyama et al. | |
| 6,409,876 B1 | 6/2002 | McQuarrie et al. | |
| 6,432,205 B1 | 8/2002 | Lee et al. | |
| 6,451,692 B1 | 9/2002 | Derderian et al. | |
| 6,492,261 B2 | 12/2002 | Gavish et al. | |
| 6,627,538 B2 | 9/2003 | Gavish et al. | |
| 6,638,580 B2 | 10/2003 | Gavish | |
| 6,751,516 B1 | 6/2004 | Richardson | |
| 6,822,245 B2 | 11/2004 | Muto et al. | |
| 7,370,932 B2 * | 5/2008 | Silverbrook et al. | 347/19 |
| 8,394,454 B2 * | 3/2013 | Kruger et al. | 427/248.1 |
| 2001/0000160 A1 | 4/2001 | Schwaiger et al. | |
| 2002/0033229 A1 * | 3/2002 | Lebouitz et al. | 156/345 |
| 2002/0084426 A1 * | 7/2002 | Gerlach et al. | 250/492.1 |
| 2002/0197851 A1 | 12/2002 | Gavish et al. | |
| 2004/0016403 A1 | 1/2004 | Gavish | |
| 2004/0020434 A1 | 2/2004 | Gavish et al. | |
| 2004/0033425 A1 | 2/2004 | Koops et al. | |
| 2004/0108458 A1 * | 6/2004 | Gerlach et al. | 250/311 |
| 2005/0016956 A1 * | 1/2005 | Liu et al. | 216/67 |
| 2006/0022136 A1 | 2/2006 | Moore | |
| 2009/0087564 A1 | 4/2009 | Horiuchi et al. | |
| 2009/0223451 A1 | 9/2009 | Kruger et al. | |
| 2011/0272592 A1 * | 11/2011 | Kellogg et al. | 250/396 R |
| 2012/0156363 A1 | 6/2012 | Quinn et al. | |
| 2012/0312236 A1 * | 12/2012 | LoBue | 118/727 |

OTHER PUBLICATIONS

R.M. Langford, D. Ozkaya, J. Sheridan and R. Chater, Effects of Water Vapour on Electron and Ion Beam Deposited Platinum, Microsc Microanal 10 (Suppl 2), 2004.

Webster's Ninth New Collegiate Dictionary, 1986, p. 391.

FEI Company, Nova 600 NanoLab DualBeamTM-SEM/FIB, Document 032-DS20111, Aug. 2003.

* cited by examiner

US 9,097,625 B2

GAS INJECTION SYSTEM FOR ENERGETIC-BEAM INSTRUMENTS

CLAIM FOR PRIORITY

This application claims the priority of U.S. Provisional Patent Application Ser. No. 61/671,473, filed Jul. 13, 2012, which application is incorporated in its entirety by reference into the present application.

CO-PENDING APPLICATIONS

This application is related to co-pending application Ser. No. 13/357,741, filed Jan. 25, 2012.

BACKGROUND

1. Technical Field

This disclosure relates to the removal of specimens inside energetic-beam instruments, such as focused ion beam (FIB) microscopes and the preparation of specimens for later analysis in the transmission electron microscope (TEM) and elsewhere, and apparatus to facilitate these activities.

2. Background

The use of in situ lift-out (INLO) for TEM sample preparation in the dual-beam FIB has become a popular and accepted technique. The INLO technique is a series of FIB milling and sample-translation steps used to produce a site-specific specimen for later observation in a TEM or other analytical instrument. Removal of the lift-out sample is typically performed using an internal nanomanipulator in conjunction with the ion-beam assisted chemical-vapor deposition (CVD) process available with the FIB tool. A suitable nanomanipulator system is the Omniprobe AutoProbe 300, manufactured by Omniprobe, Inc., of Dallas, Tex. Details on INLO methods may be found in the specifications of U.S. Pat. Nos. 6,420,722 and 6,570,170. These patent specifications are incorporated into this application by reference, but are not admitted to be prior art with respect to the present application by their mention in the background.

Gas chemistries play an important role in INLO. Gas injection in the FIB may be used for etching to speed the milling process, for ion or electron-beam assisted CVD of oxides, metals and other materials, for deposition of protective layers, and for deposition of planarizing material, such as silicon dioxide, to fill holes where lift-out samples have been excised. For a number of reasons, gas injection systems mounted on the wall of the FIB vacuum chamber have become preferred. This offers a safety advantage over injection systems using gas sources or bottled gases that are external to the FIB vacuum chamber. Chamber-mounted injection systems also permit whole-wafer analysis and can be easily inserted to place a gas nozzle near (within 50 μm) the position where the charged particle beam strikes the sample. After completion of the injection process, the system can be retracted to a safe position for normal FIB sample translation operations. An example of a gas injection system is disclosed in US Patent Publication No. 2009/0223451. This patent specification is incorporated into this application by reference, but is not admitted to be prior art with respect to the present application by its mention in the background.

There are a growing number of gas chemistries of interest and researchers typically require more than one chemistry on the same instrument. This is commonly achieved by installing additional gas injection systems that use up additional ports on the instrument. Each gas injection system has to be customized to suit the instrument and port and reagent being used. For example, there may be an "inappropriate" port on a certain instrument that, although unoccupied and thus available for mounting a gas injection system, would orient a gas injection system at an angle that would adversely affect the gas injection system's performance (e.g. allowing flow of a liquid source into the delivery path, resulting in release of a liquid undesirably into the instrument vacuum chamber). Thus there are a limited number of appropriate ports on a typical FIB, and a growing number of desired accessories that may need to be installed on these ports. Therefore, providing additional gas chemistries will not only be costly, but can also compromise the flexibility for a researcher to use other accessory instrumentation. A solution is required that can be easily adapted for use on a variety of energetic beam instruments and which offers the researcher a safe and efficient way to use more than one gas chemistry without compromising the other uses of the microscope.

DRAWINGS

DETAILED DESCRIPTION

Figure 1:
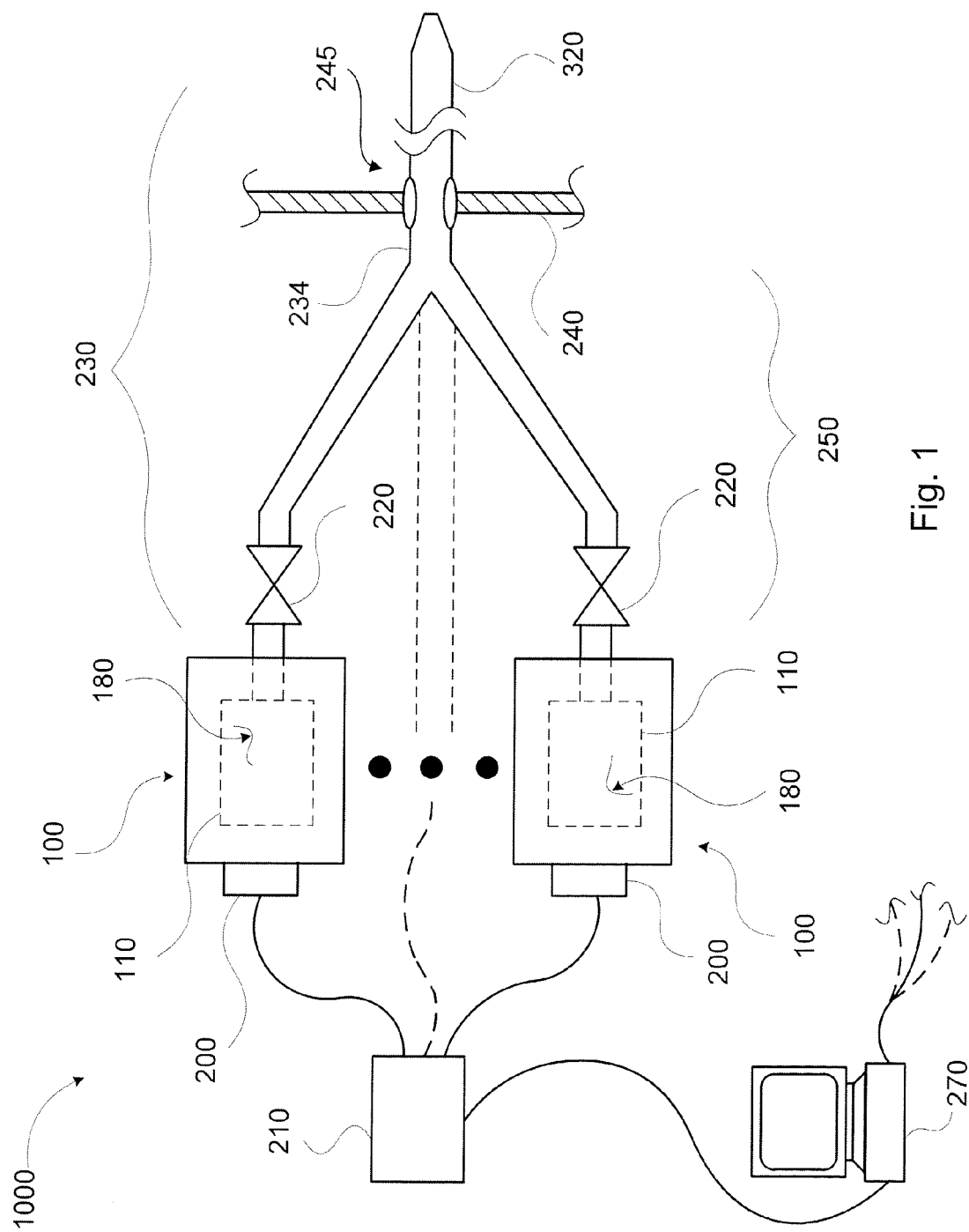
FIG. 1 is a schematic diagram of the connection of cartridges to a gas injection system.

This disclosure relates to a multiple gas source chamber-mounted injection system that only requires use of a single port and can be installed on a variety of different instruments and ports with a variety of angles. To save interrupting experiments, sources can be exchanged even while the instrument is evacuated and safety is assured by automatic recognition of the source type. Not only does the usage efficiency of existing ports improve, but with a multiple gas source chamber-mounted injection system, a complex and automated process flow, or schedule, involving different gas sources over a timed deposition period is possible. The individual sources can be maintained at different temperatures to maintain the desired vapor pressure in each tube, and feedback from sensors can be used to adjust the deposition parameters and maintain them within the correct limits.

Removable cartridges for gas sources that can be exchanged quickly and easily offer several advantages. They allow a multitude of sources to be offered on a single gas injection system, require only a single port on the vacuum chamber for the delivery of multiple gases, and broaden the range of sources quickly available beyond the number that may by physically mounted and residing on the gas injection system at any one time. This adds additional flexibility and the capability to meet a multitude of gas injection needs without consuming additional space either on the gas injection system (for more resident gas sources) or on the vacuum chamber (for more gas injection systems), and reduces the need to purchase additional energetic-beam microscope instruments. Further, research capacity is expanded without requiring the purchase of a second gas injection system, offering additional economic advantages. The inclusion of an auto-identification capability for gas source cartridges facilitates plug and play functionality. Auto identification can reduce or eliminate the requirement for operator interaction to manually adjust the controller to accommodate a source change, and enhances safety by eliminating the opportunity of operator error when manually adjusting the controller. If cartridges are mounted in different positions on the gas injection system, the auto-identification feature, when used with proper control software, can help ensure that the correct gas flows when called for in a stored recipe, regardless of the actual position of its cartridge on the system.

To fully enable a removable cartridge solution, it is advantageous to change sources rapidly. Enabling the exchange of removable cartridges while the energetic beam microscope is under vacuum helps to achieve this goal. Gas injection systems that mount directly to an energetic beam microscope commonly require venting the microscope to gain access to the gas sources. This is because existing conventional chamber-mounted systems are deliberately designed so that gas sources are always connected to the vacuum in the chamber while the gas injection system is mounted. In some existing systems, the gas chemistry reservoir itself resides inside the vacuum chamber. In this case, adding, removing, or exchanging gas reservoirs requires opening the chamber, which not only can cause significant downtime (anywhere from 10 minutes to 24 hours depending on the size of the chamber and baseline vacuum level desired), but can also result in undesirable contamination of the chamber from opening the chamber to atmosphere. Contamination leads to even more downtime as the chamber is cleaned, or alternately, may deleteriously affect the quality of the experiment if the chamber is not cleaned. Herein the term vent-free refers to the capability of changing cartridges without venting the vacuum chamber (opening it to the atmosphere). Vent-free embodiments, as provided herein, enable plug and play functionality while eliminating the negative repercussions from venting the energetic-beam microscope.

Figure 2:
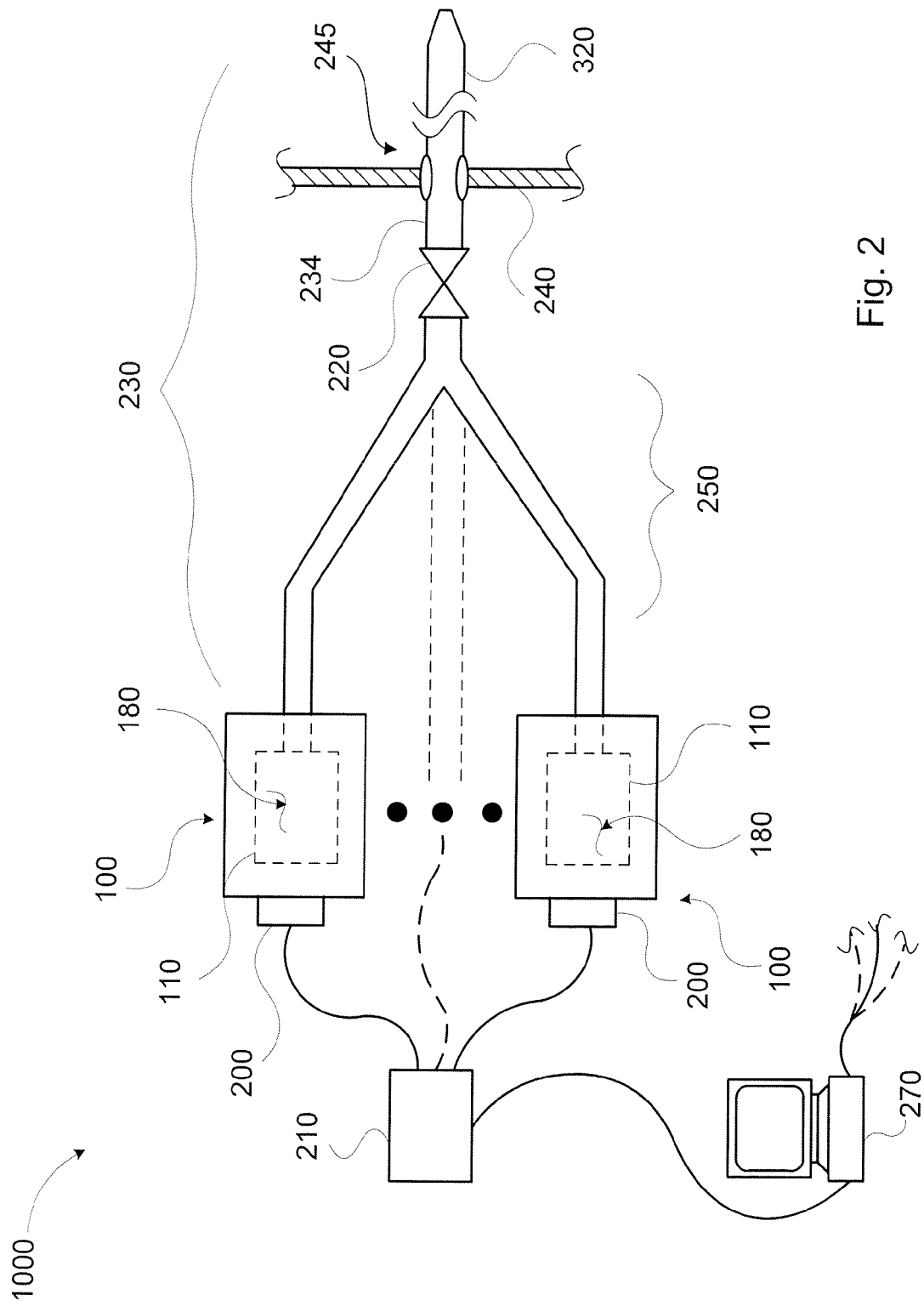
FIG. 2 is a schematic diagram of another embodiment of a gas injection system.

Referring now to FIG. 1, a gas injection system (1000) is provided comprising cartridges (100) capable of holding chemicals (180) or chemical precursors that serve as sources for gases that will be delivered into the vacuum chamber (240) of an energetic-beam instrument, such as a focused ion beam microscope (FIB) or scanning electron microscope (SEM). FIG. 1 shows the general layout of the cartridges (100) of an embodiment. One or more cartridges (100) are connected through isolation valves (220) to a delivery path (230). The delivery path (230) is shown here as including a manifold (250) converging to a single delivery line (234) that enters the vacuum chamber (240) of the instrument at a port (245) in the vacuum chamber (240), and terminates inside the vacuum chamber in a nozzle (320) for delivering the output gas to a sample in the vacuum chamber. This configuration allows the output gases from one or more cartridges to be mixed as desired and/or delivered by nozzle (320) to the same area of a sample. Each cartridge (100) has internal valving (discussed below) and a reservoir (110) for holding a chemical (180) or chemical precursor capable of serving as a source of an output gas, each called a "chemical" here. Each cartridge (100) also has an identification device (200) connected to a recognition device (210), so that characteristics of a given cartridge (100) such as the identity of its contents may be identified to a controller (270), here drawn as a programmable computer, for control of processes (discussed below). FIG. 2 is a schematic diagram of an alternative embodiment having one isolation valve (220) in the delivery path (230) instead of one per cartridge (100).

Figure 3:
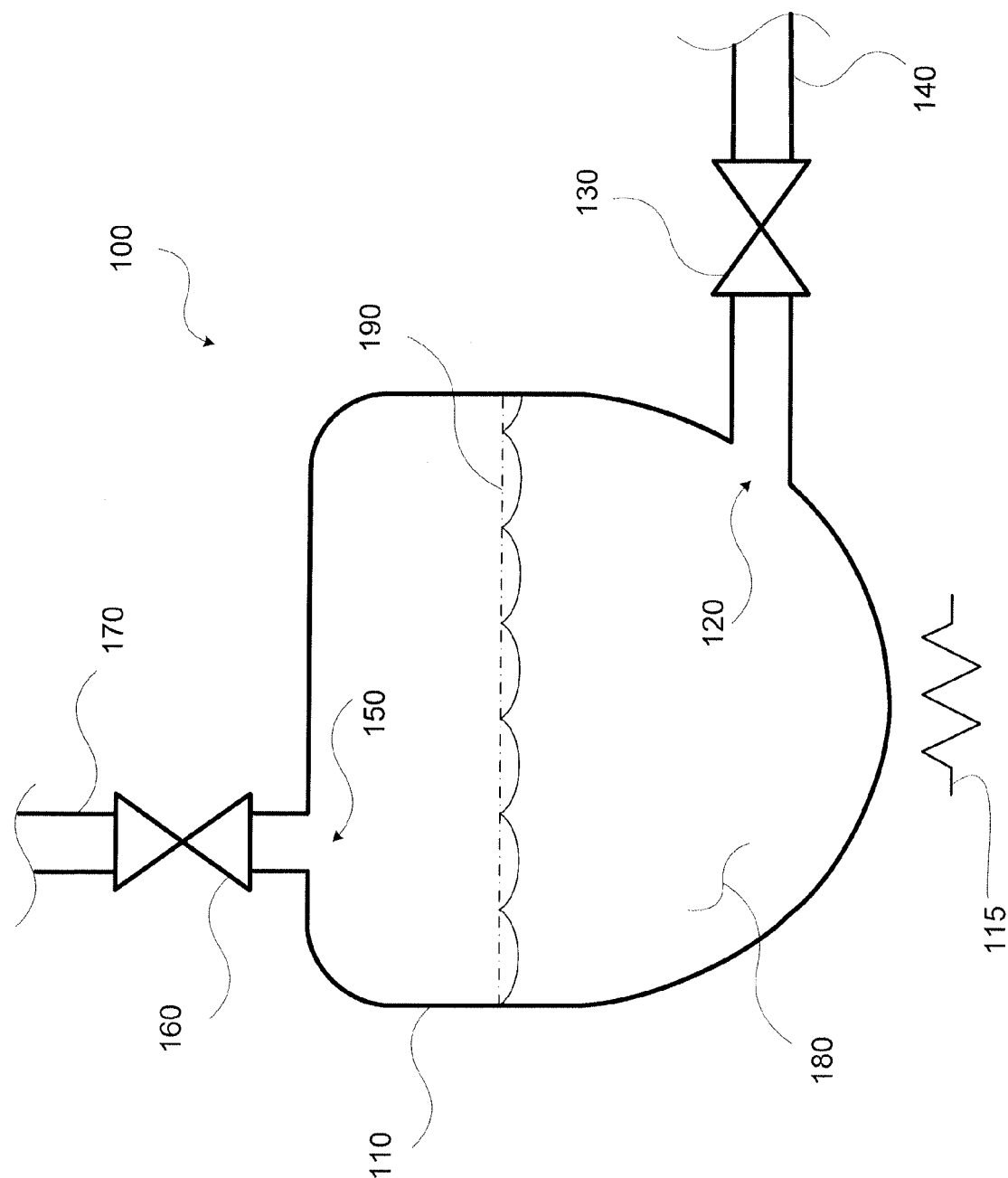
FIGS. 3 through 5 show details of a cartridge holding liquid or fine powder at different orientations.
Figure 4:
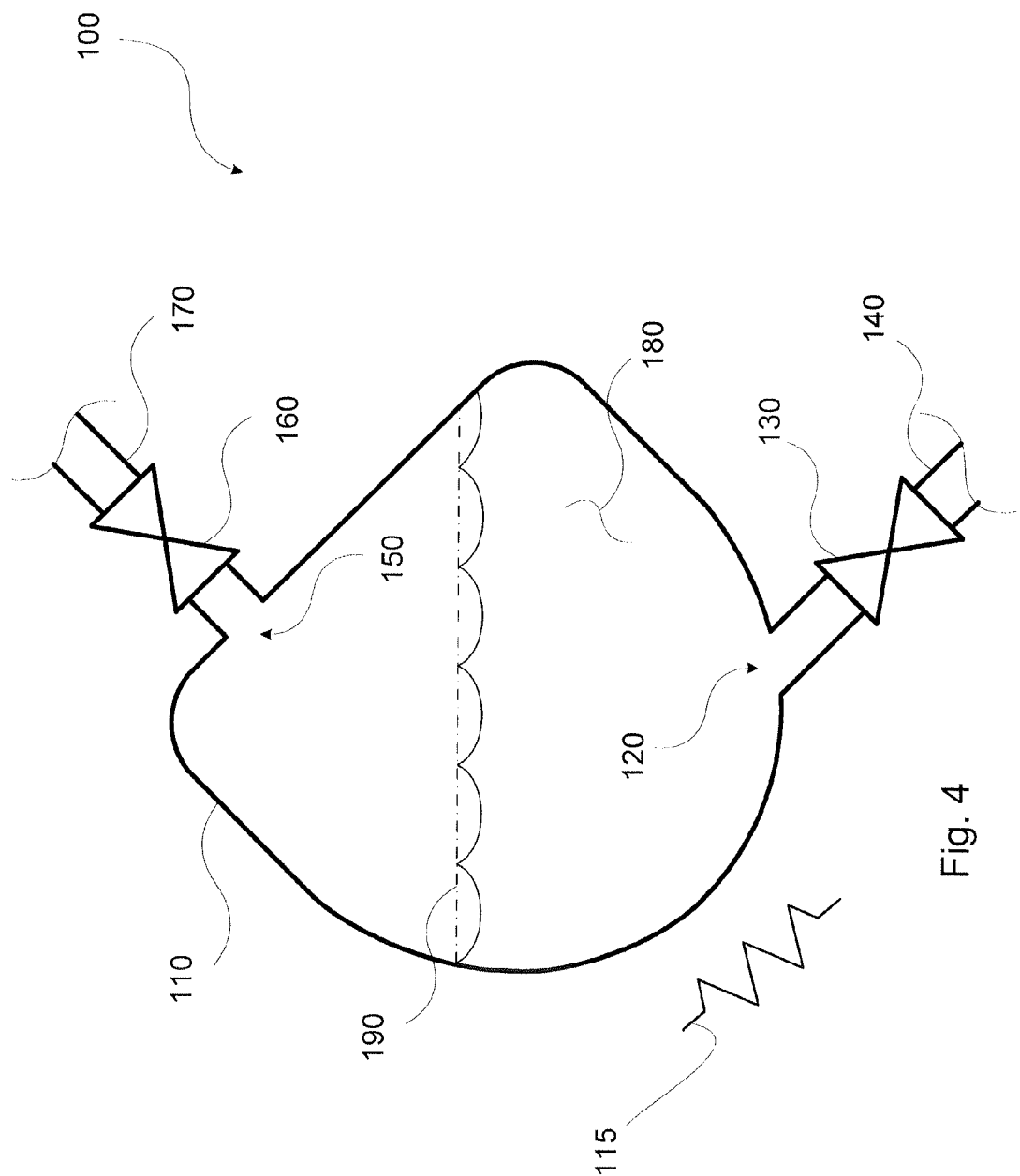
Figure 5:
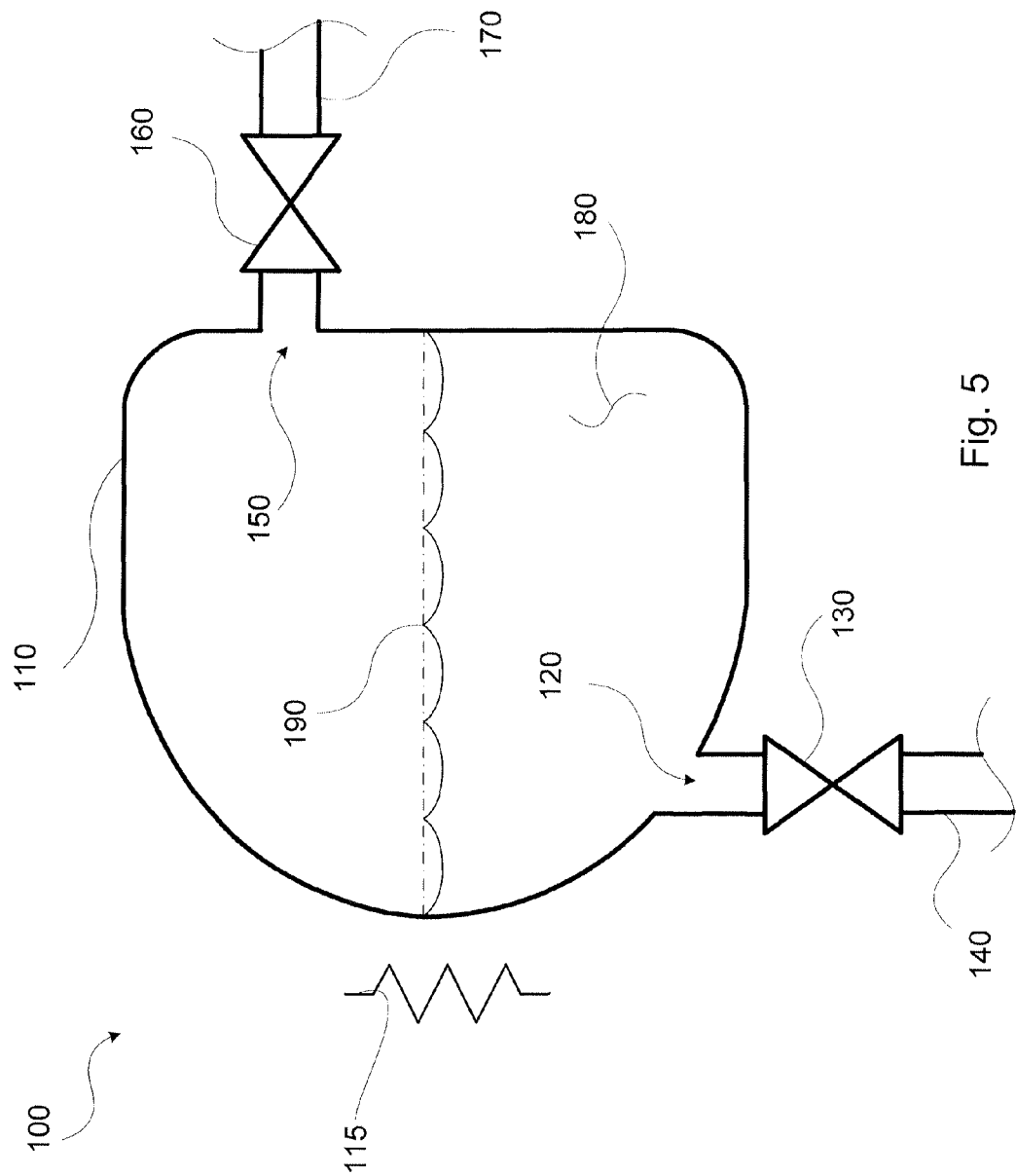

FIGS. 3 through 5 show details of a cartridge (100) holding chemical (180) in the form of a liquid or fine powder at different orientations. The reservoir (110) of each cartridge (100) has an inlet (120) coupled to an input valve (130). The input valve (130) is coupled to an input passage (140) for the selective input of carrier gases. The input valve (130) can be a controllable input metering valve, or can include an additional input metering valve. The reservoir is preferably connected to a heater (115) for heating the chemical (180) contents. Additional heaters may be distributed throughout the gas injection system (1000) for controlling the distribution of temperatures along the delivery path (230).

The reservoir (110) has an outlet (150) for the output of the chemical (180), possible mixed with a carrier gas. The outlet (150) is connected to an output valve (160) and from that point to an output passage (170). This output valve (160) can be a controllable output metering valve, or can include an additional output metering valve. As shown in FIG. 1, the output passage is further connected to an isolation valve (220) for the purpose of selectively isolating the cartridge (100) from the atmosphere within the vacuum chamber (240) of the instrument.

The reservoir (110) may have a separate port (not shown) for filling with chemical (180) prior to use in the gas injection system (1000), or the reservoir may be filled through the input passage (140) or the output passage (170).

Figure 12:
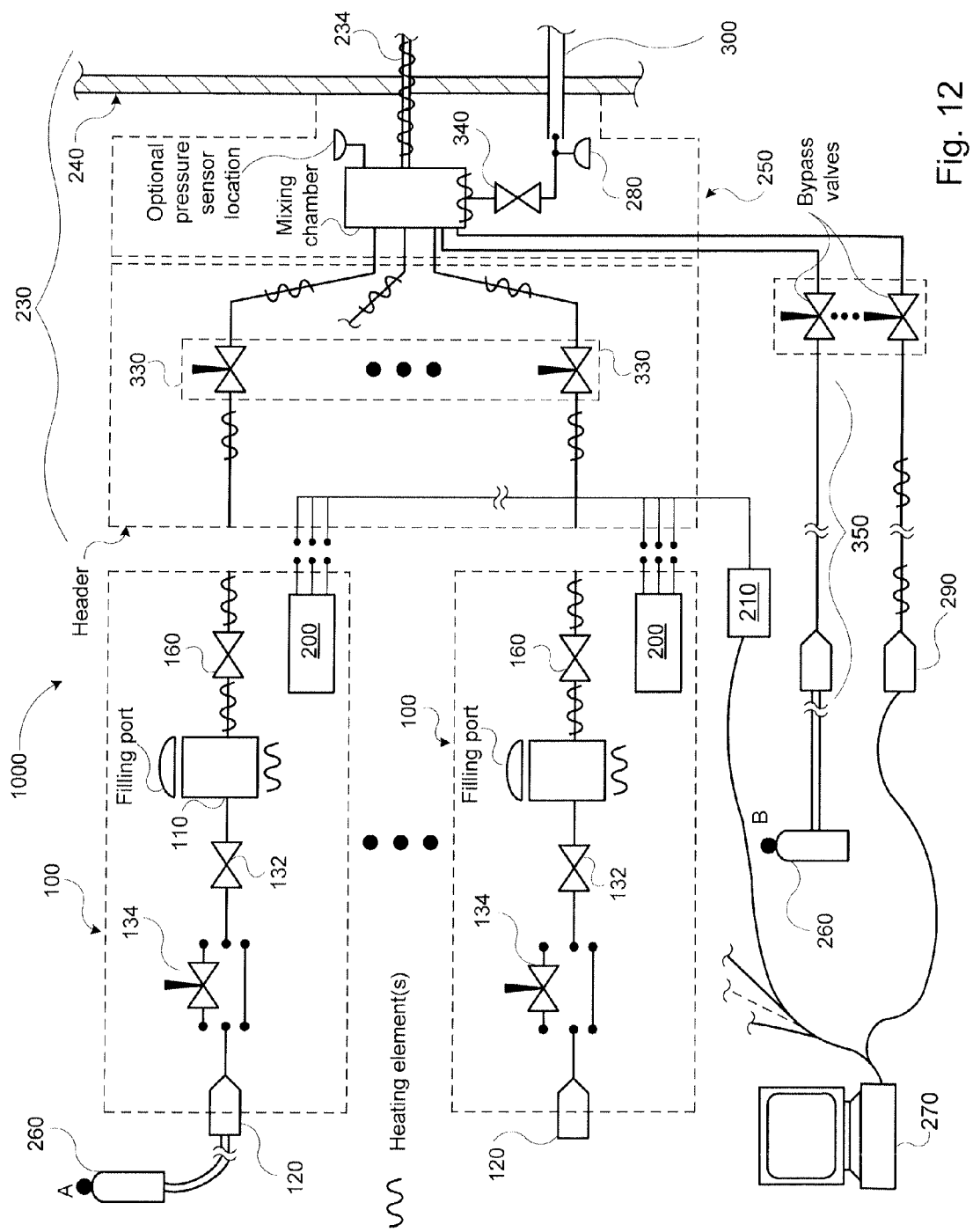
FIG. 12 is a schematic diagram of a complete gas injection system, according to the present disclosure.

The chemical (180) in the reservoir (110) rises to a fill line (190), usually predetermined by the amount of chemical (180) previously placed into the reservoir (110). The inlet (120) and outlet (150) of the cartridge (100) are disposed so that at the various tilt angles shown in the drawings (FIGS. 3 through 5), the outlet (150) remains above the fill line (190), so that a chemical (180) in liquid or fine powder form is prevented from directly entering the vacuum chamber (240) while the desired output gas is delivered to the vacuum chamber (240). In general, the reservoir (110) is capable of being heated to cause the chemical (180) to vaporize and, possibly joining with a carrier gas from the inlet (120), to flow into the outlet (150). In this way, the bulk chemical (180) does not enter the outlet (150) and the vacuum chamber (240), only the output gas, which is possibly combined with a carrier gas that enters the gas injection system through an input passage (140) of a cartridge (100) or perhaps through an auxiliary carrier gas input path (350) as shown in FIG. 12. It is generally preferable, but not essential, that inlet (120) be disposed to remain below fill line (190) at various tilt angles in order to allow an input gas to flow through the chemical (180).

Figure 6:
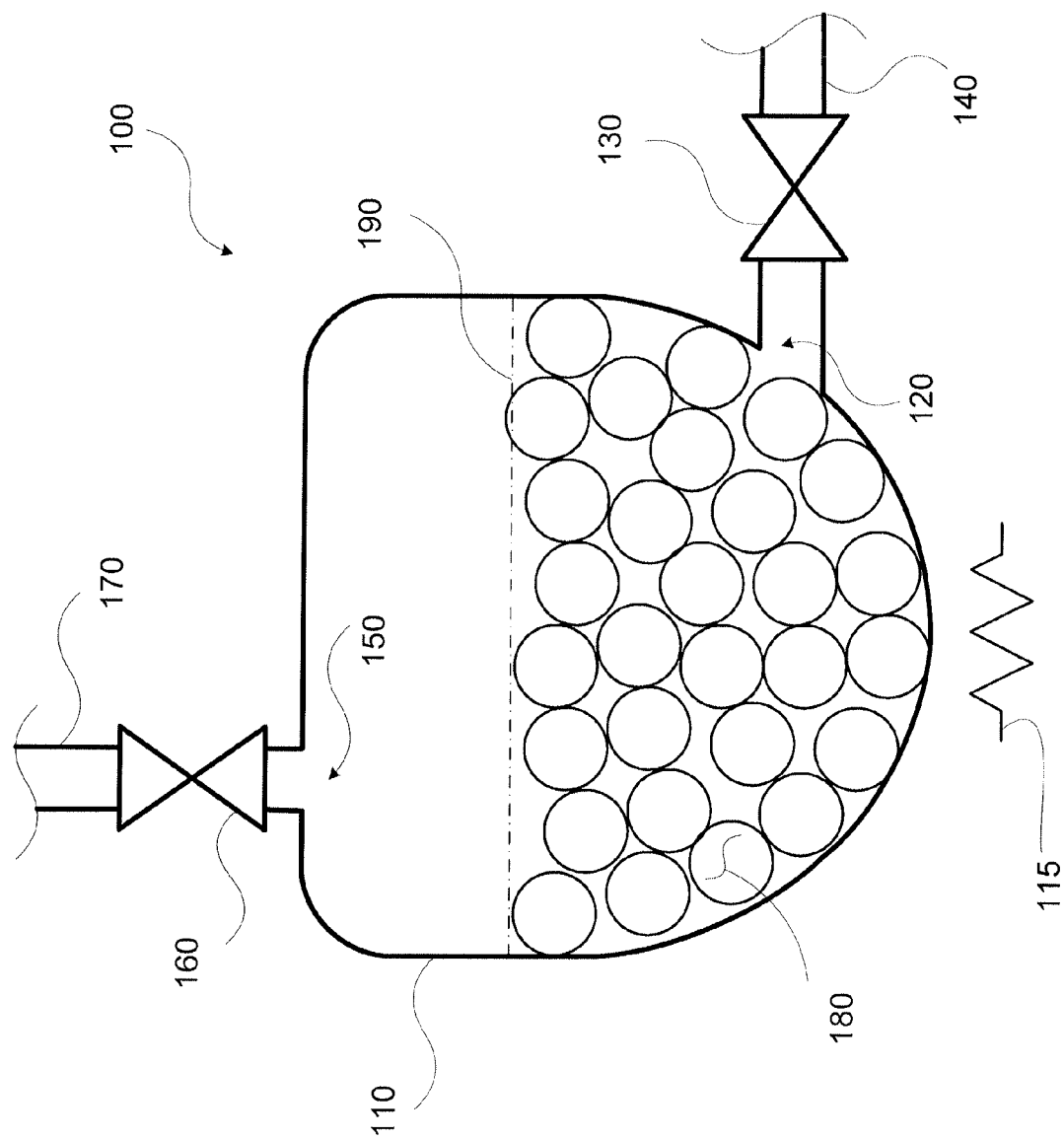
FIGS. 6 through 8 show details of a cartridge holding pellets of a chemical at different orientations.
Figure 7:
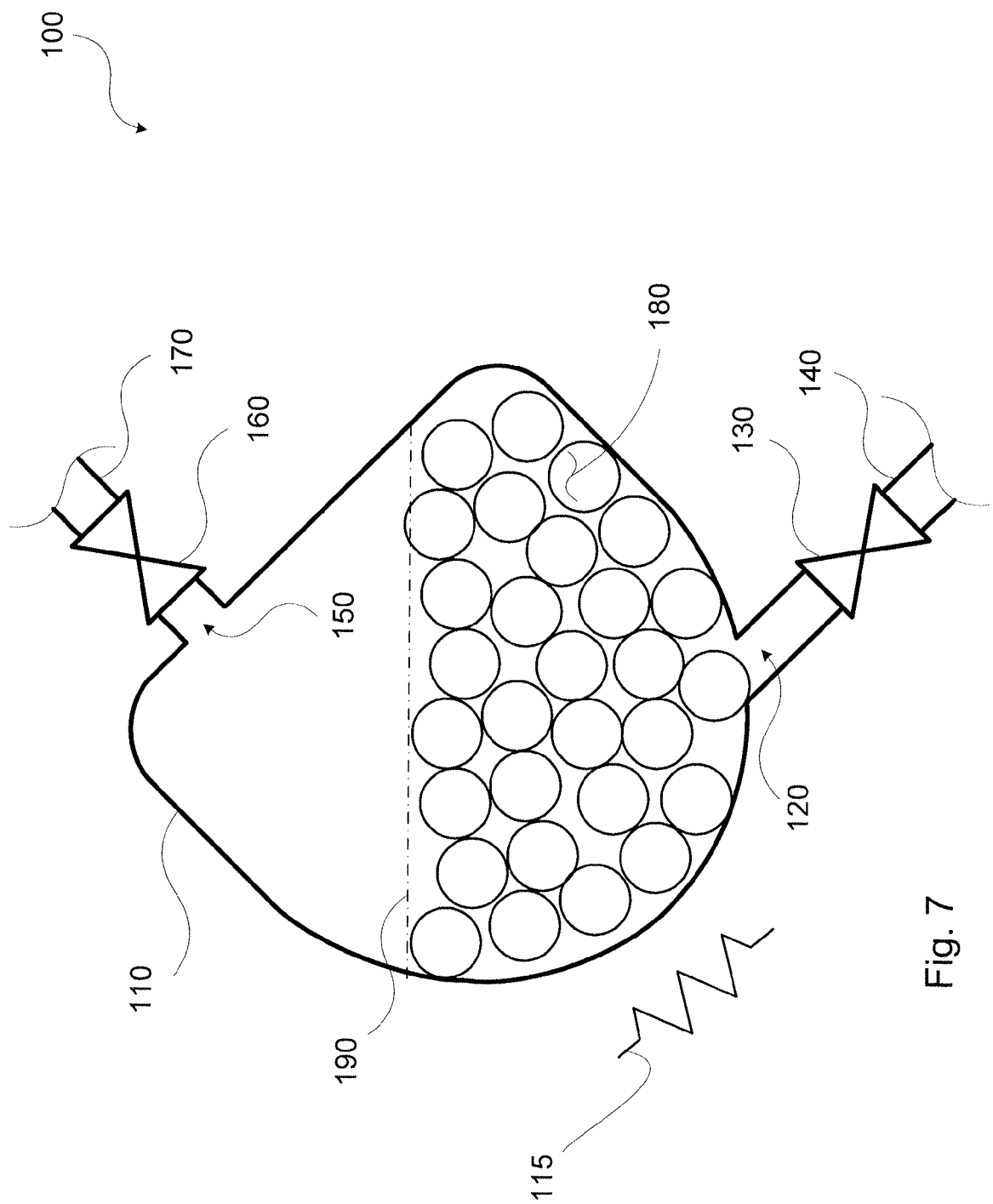
Figure 8:
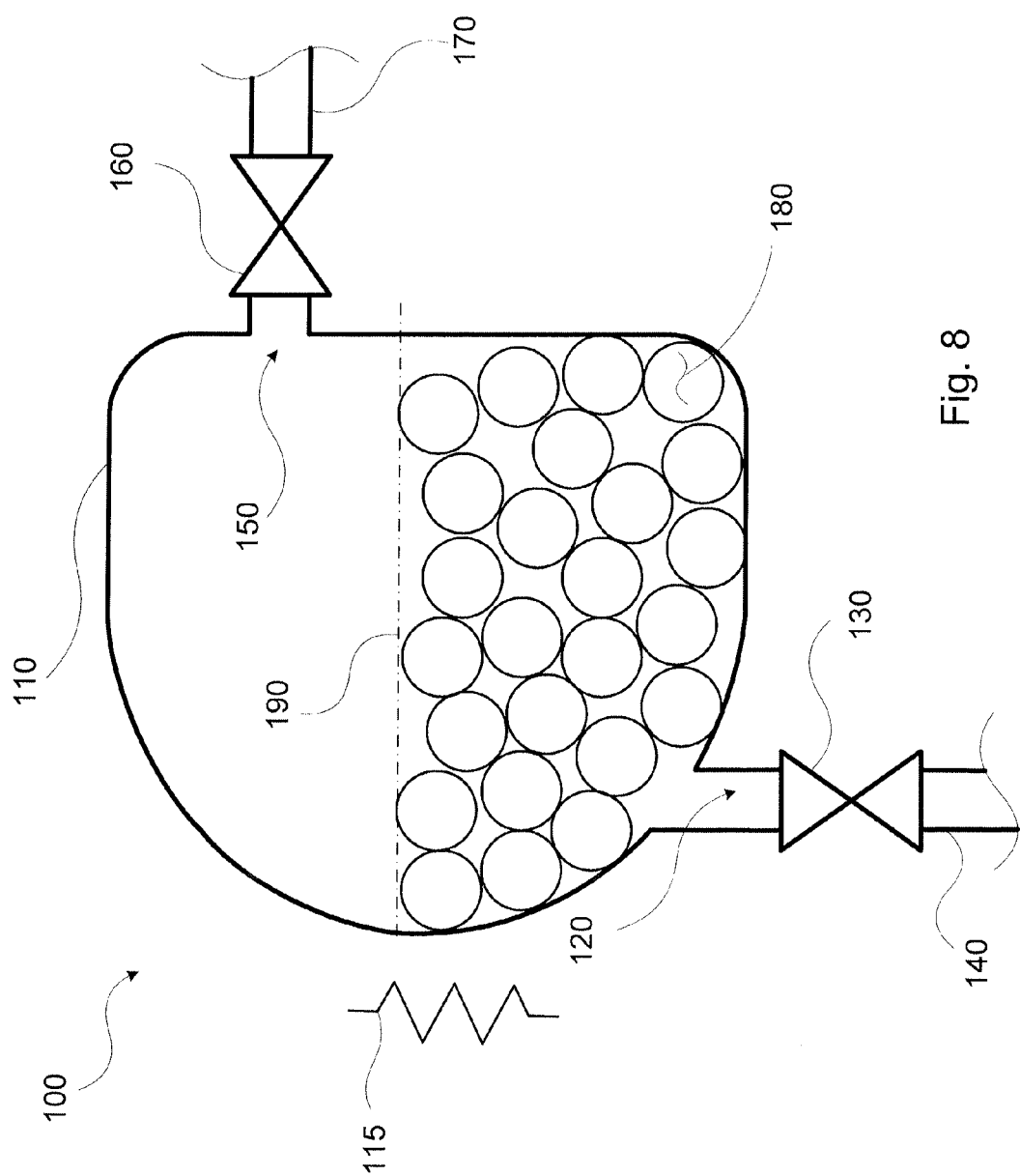

The reservoir (110), or the chemical (180) within the reservoir, can serve as a source for an output gas in any one of a variety of ways, as will be appreciated by those skilled in the art. For example, FIGS. 6 through 8 show a similar arrangement of the cartridge (100), where the chemical (180) comprises relatively large pellets. Such large pellets can be composed of a material that has a nanoporous large surface area that can adsorb and retain a useful amount of output gas at room temperature, and that when heated can desorb the output gas at a useful vapor pressure for delivery. This technology has been developed for safe storage and delivery of toxic gases into semiconductor processing equipment. A commercially available deposition precursor source in the form of nanoporous pellets is exemplified by the SAGE™ (Sub-Atmospheric Gas Enhanced) technology developed by ATMI, Danbury, Conn. These pellets also define a fill line (190), which remains below the outlet (150) as the cartridge (100) is tilted.

Figure 9:
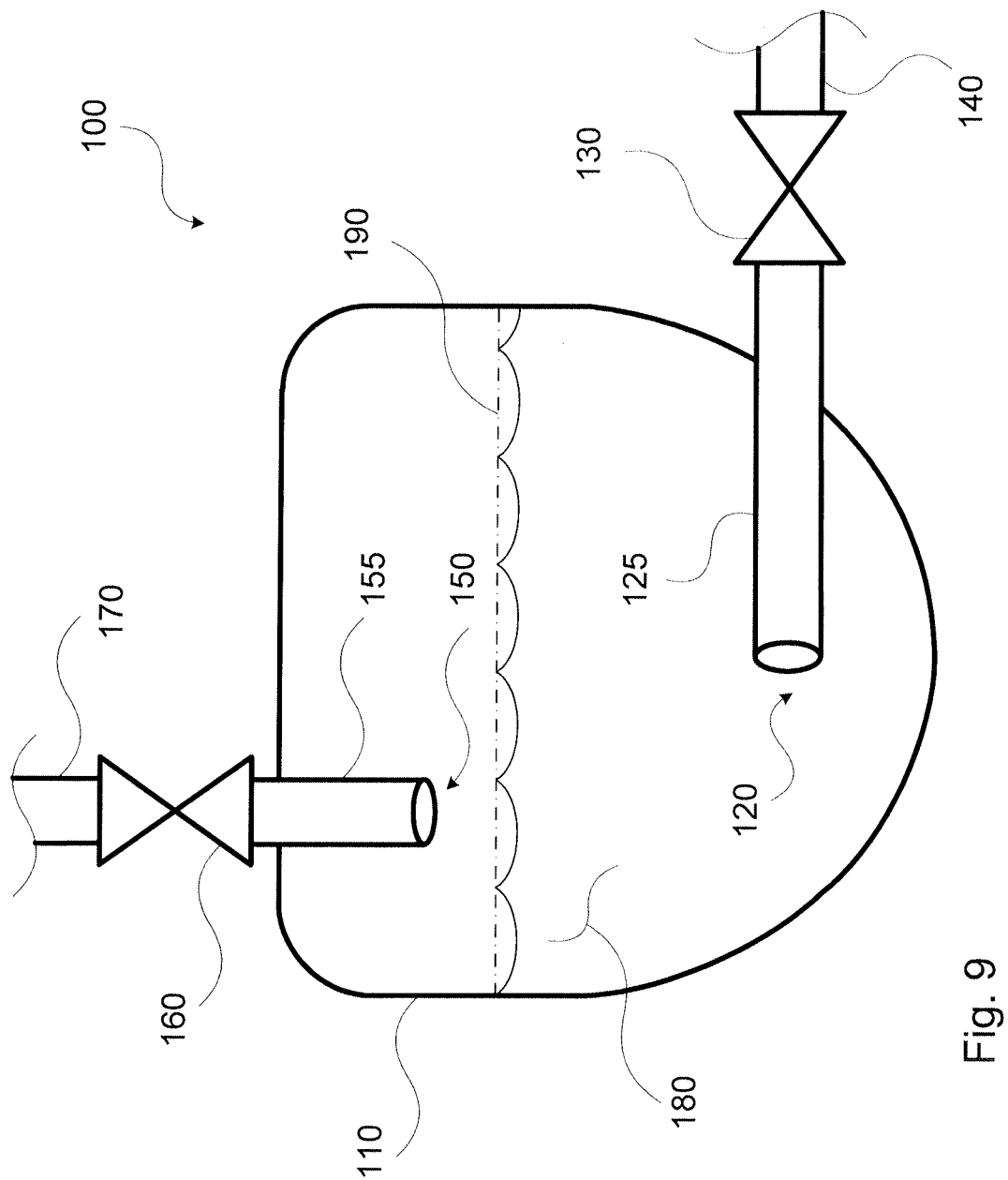
FIGS. 9 through 11 show another embodiment of the cartridge at different orientations.
Figure 10:
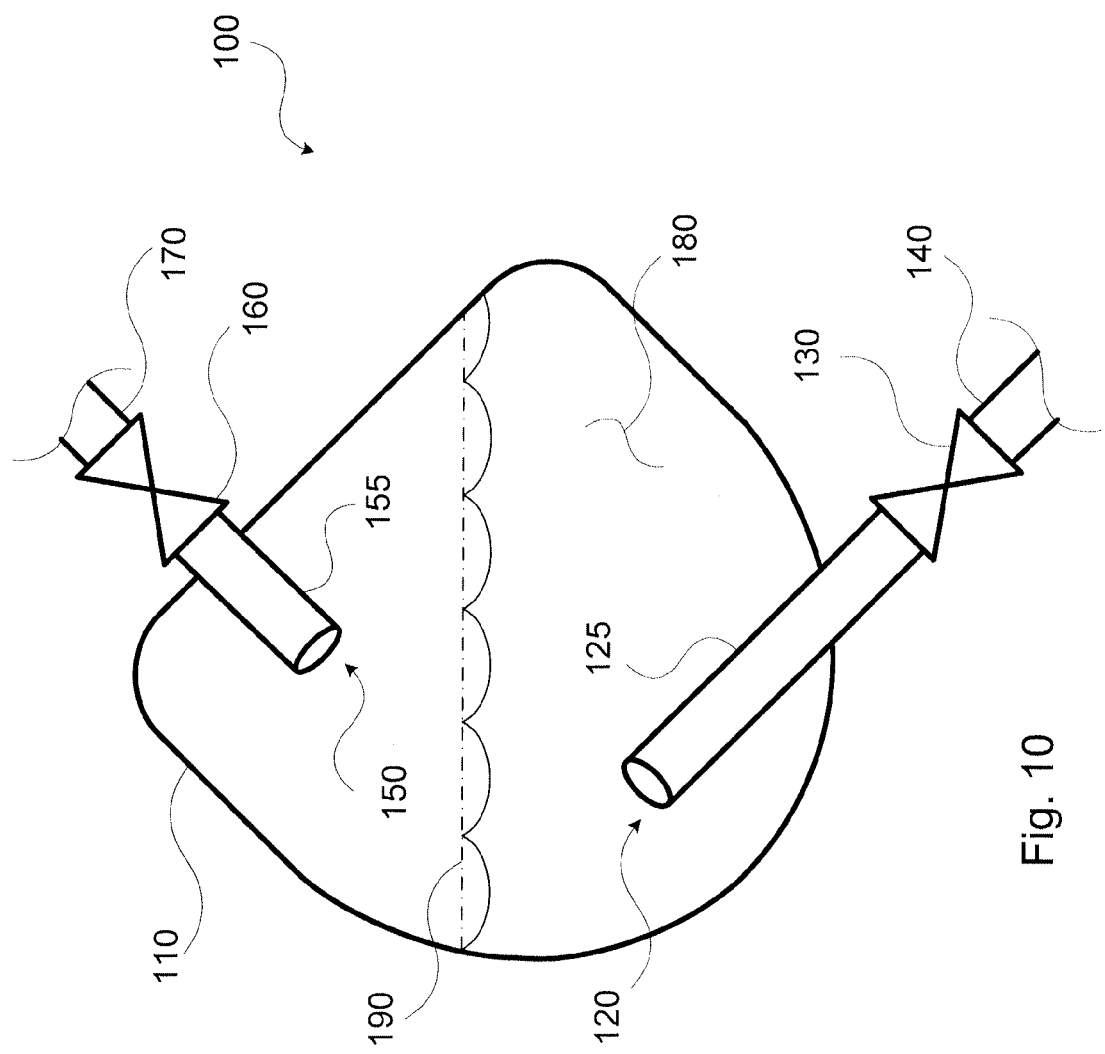
Figure 11:
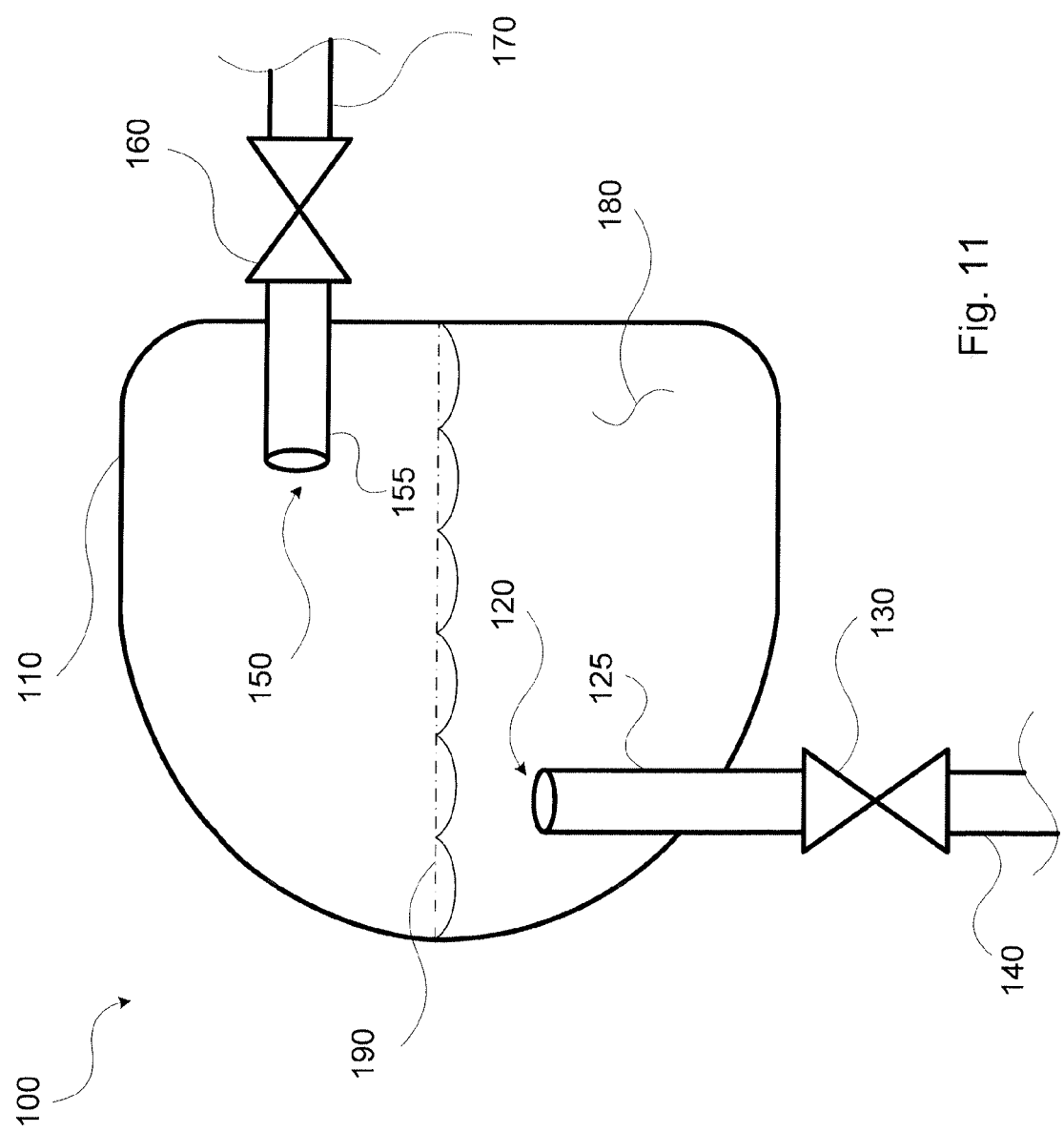

FIGS. 9 through 11 show an alternative embodiment, where the inlet (120) and outlet (150) further comprise an inlet dip tube (125) and an outlet dip tube (155). It will be apparent to those skilled in the art that dip tubes or other devices or structures having an inlet (120) or outlet (150) may be used, so long as the inlet (120) and especially the outlet (150) remain disposed as described above. It will also be apparent that the same type of device or structure need not be used for both inlet (120) and outlet (150).

Figure 14:
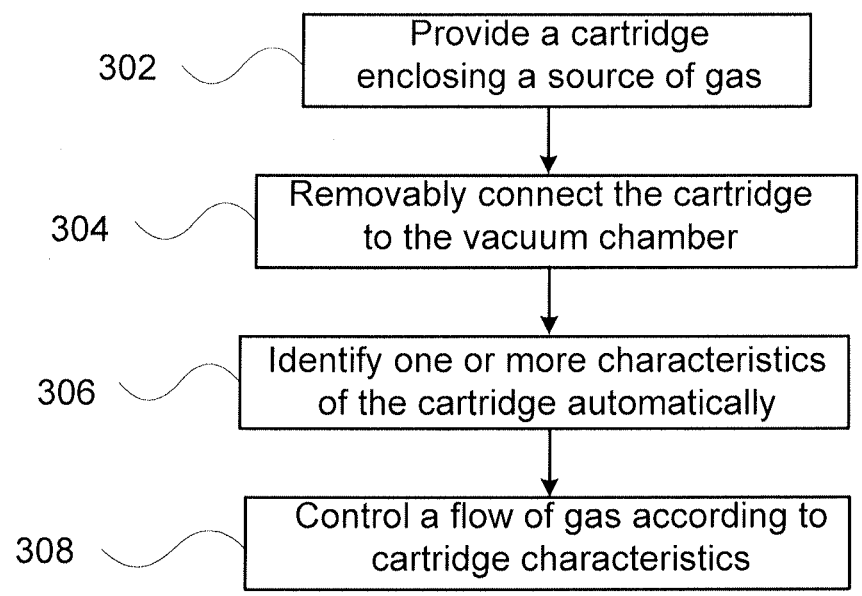
FIGS. 14 and 15 are flow charts showing methods of operating the gas injection system.
Figure 15:
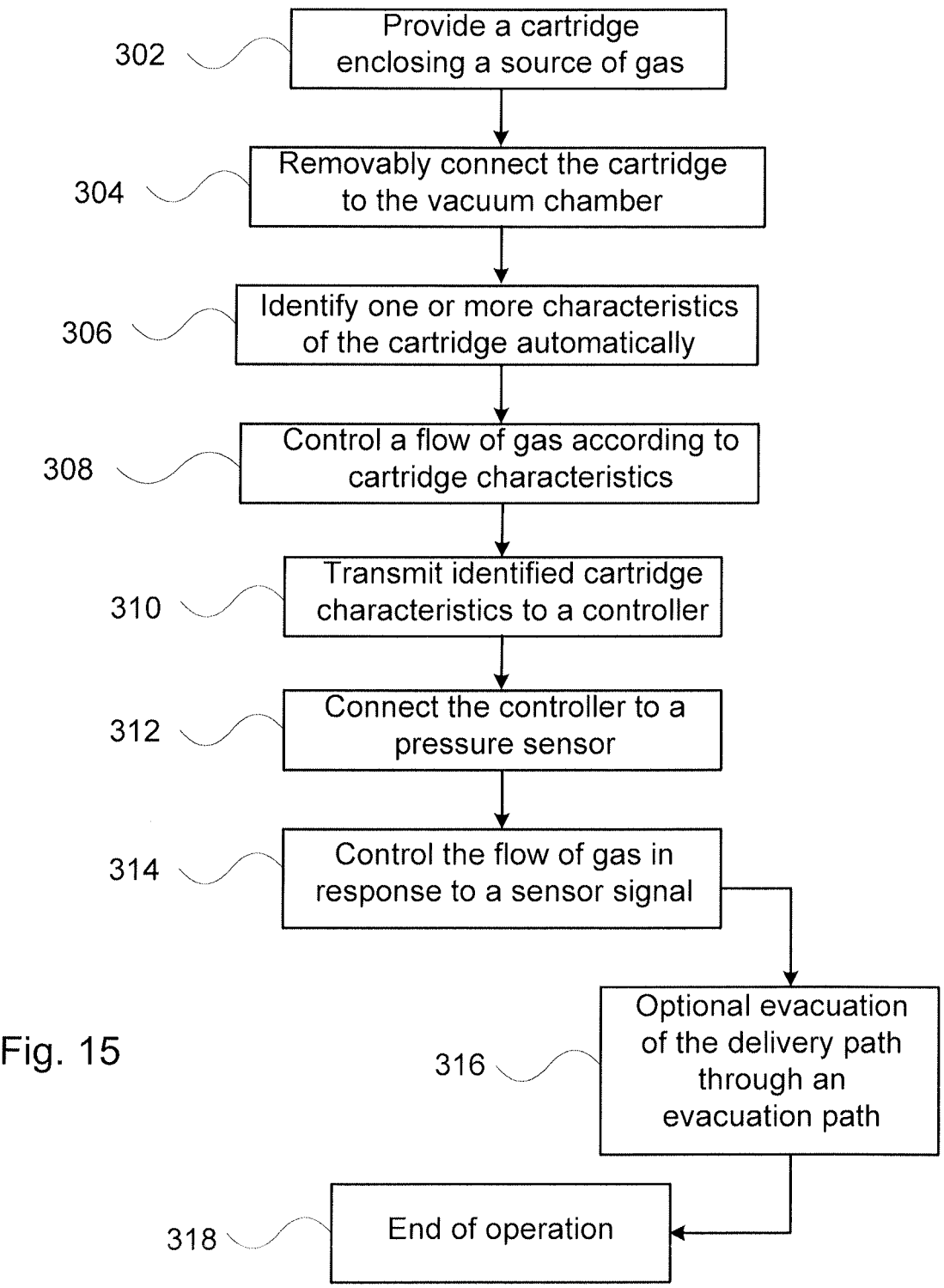

FIG. 14 shows a flow chart of a method for supplying a gas according to cartridge (100) characteristics. In step 302, the user provides a cartridge (100) enclosing a source of gas; in step 304 the cartridge (100) is removably connected to the vacuum chamber (240) at a port (245) as described above, through the mechanisms of the gas injection system (1000). In step 306, one or more characteristics of the cartridge (100) are automatically identified, and in step 308 the gas injection system (1000) controls a flow of gas according to the cartridge (100) characteristics. FIG. 15 shows further detailed steps in the method, including some optional steps. At step 310 the gas injection system (1000) transmits cartridge (100) characteristics to a controller (270). At step 312 the controller (270) is optionally connected to a pressure sensor (280). At step 314, the flow of gas may be controlled in response to a sensor signal. At step 316 there may be optional evacuation of the delivery path through an evacuation path (300).

Figure 13:
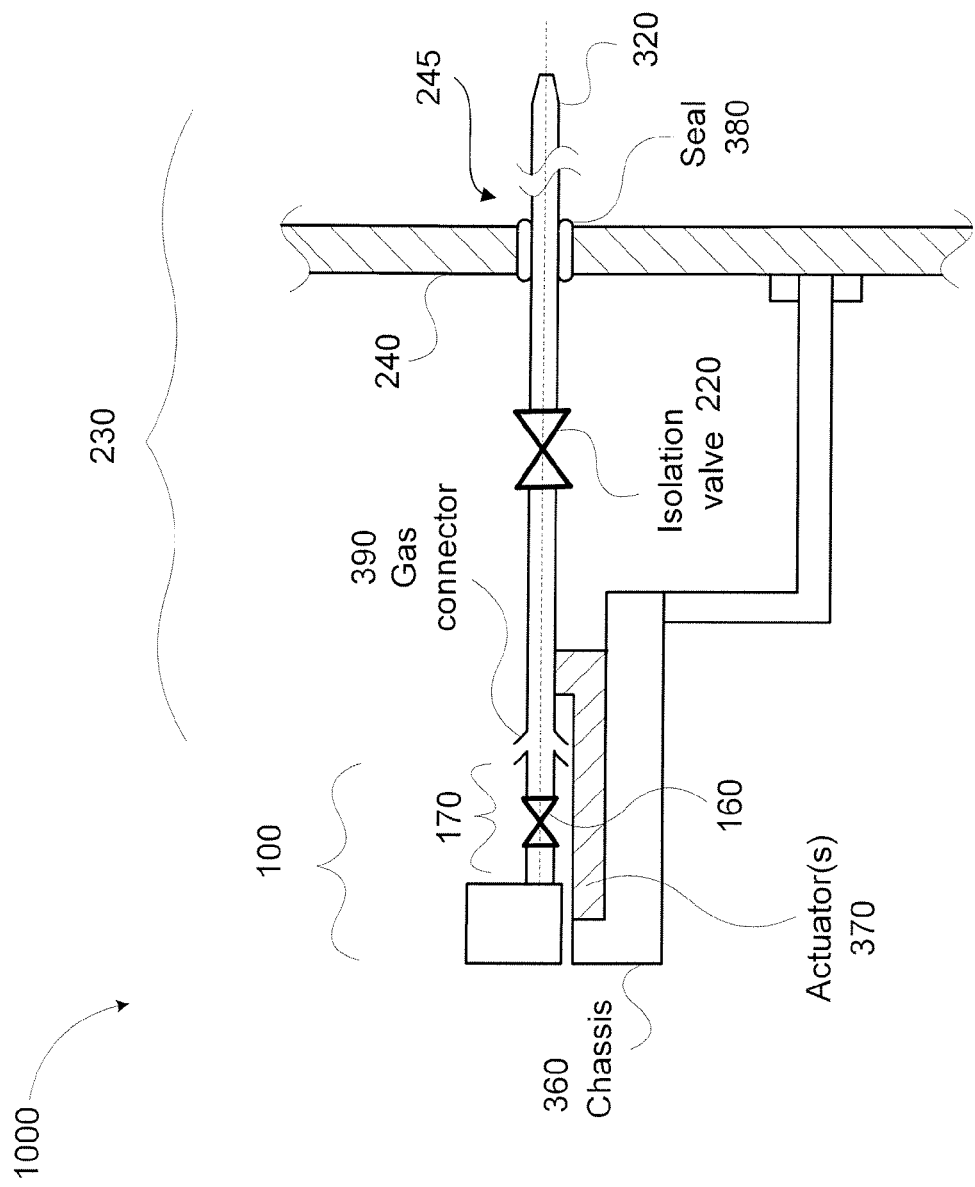
FIG. 13 is a schematic structural diagram of the gas injection system mounted to the vacuum chamber wall of an energetic-beam instrument.

FIGS. 12 and 13 show an embodiment of the gas injection system (1000) for an energetic-beam instrument having a vacuum chamber (240), where the gas injection system (1000) comprises a chassis (360) mounted to the vacuum chamber (240) at a port (245); a removable cartridge (100) supported upon the chassis (360) and having an interior and an exterior, and capable of containing a chemical (180) serving as a source for an output gas, the removable cartridge (100) comprising an output passage (170) through which the output gas may flow from the interior to the exterior of the cartridge (100); a delivery path (234) having a conductance and connecting the output passage (170) of the removable cartridge (100) to the vacuum chamber (240), through which the output gas is delivered into the vacuum chamber (240); and, an isolation valve (220) in the delivery path (234), whereby the cartridge (100) may be removed while the vacuum chamber (240) remains under vacuum when the isolation valve (220) is closed.

FIG. 13 also shows the delivery path (230) terminating in a nozzle (320) for injecting the output gas into the vacuum chamber, and that the gas injection system (1000) may further comprise at least one actuator (370) coupled to the nozzle (320) for controlling the location of the nozzle (320) within the vacuum chamber (240). A seal (380) engaging the nozzle (320) at the port (245) of the vacuum chamber (240) is also shown schematically to allow the delivery path (230) to penetrate the wall of vacuum chamber (240) at the port (245) without leaking air into the vacuum chamber (240). Such a seal (380) may be implemented in one of several ways known to those skilled in the art, including O-rings or bellows, and may be configured to permit the motion of nozzle (320) within vacuum chamber (240). A gas connector (390) enables the removable cartridge (100) to be separated from the delivery path (230) for removal and replacement.

FIG. 12 is a schematic diagram of the components of an exemplary embodiment of a complete gas injection system (1000) according to the present disclosure. The gas injection system (1000) in this embodiment includes a manifold (250) in the delivery path (230). The manifold (250) is shown here optionally constructed in two pieces including a header. The gas injection system (1000) has at least one precursor valve (330) in the manifold (250) associated with at least one cartridge (100). In this embodiment, the precursor valves (330) serve both as output metering valves to control the flow of output gas in a continuously variable manner, or, the precursor valves (330) may also be shut off completely to function as isolation valves (220), whereby a cartridge (100) may be removed while the vacuum chamber (240) remains under vacuum when the associated precursor valve (330) is closed.

FIG. 12 also shows a source of input gas (260) connected through the input shutoff valve (132) to the reservoir (110) in a cartridge (100). The input passage (140) of a cartridge (100) may be configured either with a direct connection to input shutoff valve (132), or may include an optional input metering valve (134), whereby the flow of input gas into the reservoir may be controlled.

FIG. 12 further shows a controller (270) which may comprise a programmable computer, further comprising a CPU, memory, program and data storage, and input/output devices. The controller (270) is operatively connected to control the input metering valves (134), precursor valves (330), heating elements, and other variable components of the gas injection system (1000) in response to instructions, recipes, and/or feedback from sensors. For example, there may be at least one pressure sensor (280) for sensing pressure within the vacuum chamber (240), and a composition sensor (290), such as a residual gas analyzer or optical spectrometer, for sensing the composition of the atmosphere within the vacuum chamber (240). In general, the output signals from the pressure sensor (280) and the composition sensor (290) are connected to the controller (270), so that control signals can be computed to control the precursor valves (330), operating as output metering valves, according to a predetermined program of operation.

The reader should note that the controller may be any one of a programmable computer, an electronic feedback control system (which might use analog circuitry), a programmable logic controller (PLC), an embedded microcontroller, or similar devices.

Preferably, an evacuation path (300) that is selectively openable through a purge valve (340) is connected to the delivery path (230), where the evacuation path (300) has a conductance higher than the conductance of the delivery path (230), thus allowing the delivery path (230) to be evacuated when desired. The evacuation path may be connected to the vacuum chamber (240) as shown in FIG. 12, or it may be connected to a separate vacuum source such as a dedicated vacuum pump. By using a higher-conductance evacuation path, the delivery path may be evacuated more rapidly and thoroughly than by evacuating the delivery path through the nozzle (320) into the vacuum chamber (240).

As stated above, each cartridge (100) also has an identification device (200) connectable by wires or wirelessly to a recognition device (210), so that characteristics of a given cartridge (100) may be identified to the controller (270) as a further input to a program for controlling the gas injection processes. The identification device (200) may be a DIP switch, or a read-only memory, or a programmable memory, or a wireless transponder, preferably holding coded information regarding one or more characteristics of the cartridge (100), such as the identification of the chemical (180) therein contained. Various other characteristics of a cartridge (100) might be usefully identified using identification device (200). The recognition device (210) may be capable of decoding the information provided by identification device (200), or it may simply be a disconnectable hardware interface such as a connector plug, connected to the identification device (200) when the cartridge (100) is mounted in the gas injection system (1000). If the recognition device (210) is not capable of decoding the coded information itself, then it can convey the coded information through a communication connection (not shown) to a separate device such as the controller (270) to perform the decoding and interpretation and/or display of the information. The information regarding characteristics of the cartridge can then be used by controller (270) to influence the operation and control of the gas injection system (1000). For example, recipes stored in the controller (270) might be made available in response to the presence or absence of cartridges containing certain chemicals. Similarly, safe operation can be enforced by the controller by using software control of output valves or precursor valves to prevent the mixing of combinations of output gases that could react violently or produce dangerous reaction byproducts.

A recipe stored in the controller (270) can also be designed to bring the pent-up pressure down to normal levels based upon automatic recognition of the time since the cartridge (100) was last operated.

In operation, the cartridge (100) is removably connected to the vacuum chamber (240) while keeping the vacuum chamber (240) under vacuum. Through the identification device (200) and the recognition device (210), the characteristics of the cartridge (100) are automatically identified to the programmable computer (270). The pressure sensor (280) and the composition sensor (290) also generate signals communicated to the programmable computer (270), whereby the gas injection process in the vacuum chamber (240) may be controlled according to a predetermined program.

None of the description in this application should be read as implying that any particular element, step, or function is an essential element which must be included in the claim scope; the scope of patented subject matter is defined only by the allowed claims. Moreover, none of these claims are intended to invoke paragraph six of 35 U.S.C. Section 112 unless the exact words "means for" are used, followed by a gerund. The claims as filed are intended to be as comprehensive as possible, and no subject matter is intentionally relinquished, dedicated, or abandoned.

We claim:

1. A gas injection system for an energetic-beam instrument having a vacuum chamber; the vacuum chamber having at least one port; the port having a tilt angle; the gas injection system comprising:
   the gas injection system supporting at least one cartridge, each of the at least one cartridges containing a chemical source; the chemical source serving as a source for an output gas to be delivered into the vacuum chamber, each of the at least one cartridges comprising:
   a reservoir containing the chemical source, the chemical source rising to a fill line; the fill line having a level defined by an amount of the chemical source present in the reservoir at a given time,
   an output passage,
   an output valve coupled to the output passage; and,
   an outlet from the reservoir coupled to the output passage through the output valve; the outlet disposed in the reservoir at a level above the level of the fill line, and configured so that as the gas injection system is tilted to the tilt angle of the port, the outlet of each of the at least one cartridges remains above the level of the fill line, whereby the chemical source is prevented from entering the vacuum chamber while the output gas is being delivered;
   the gas injection system is configured to be removable and re-attachable to another port of a different tilt angle, whereby the chemical source is also prevented from entering the vacuum chamber while the output gas is being delivered.

2. The gas injection system of claim 1, wherein the tilt angle ranges from substantially horizontal to substantially vertical.

3. The gas injection system of claim 1, further comprising a delivery path removably coupled to the output passage.

4. The gas injection system of claim 3, further comprising an isolation valve in the delivery path, whereby the cartridge may be removed while the vacuum chamber remains under vacuum when the isolation valve is closed.

5. The gas injection system of claim 3, wherein the delivery path further comprises a manifold.

6. The gas injection system of claim 5, further comprising at least one isolation valve in the manifold associated with the at least one cartridge, whereby the cartridge may be removed while the vacuum chamber remains under vacuum when the associated isolation valve is closed.

7. The gas injection system of claim 3, wherein the delivery path terminates in a nozzle for injecting the output gas into the vacuum chamber; the nozzle having a location in the vacuum chamber.

8. The gas injection system of claim 7, further comprising an actuator coupled to the nozzle for controlling the location of the nozzle within the vacuum chamber.

9. The gas injection system of claim 1, wherein the output valve further comprises an output metering valve.

10. The gas injection system of claim 1, further comprising a source of an input gas connected through an input valve to the reservoir, whereby a flow of the input gas into the reservoir may be controlled using the input valve.

11. The gas injection system of claim 10, wherein the input valve further comprises an input metering valve.

12. The gas injection system of claim 1, further comprising a heater.

13. The gas injection system of claim 1, further comprising a controller configured such that it is capable of varying a parameter of the gas injection system, whereby the operation of the gas injection system may be controlled.

14. The gas injection system of claim 13, wherein the controller further comprises a programmable computer.

15. The gas injection system of claim 13, wherein the parameter that can be varied by the controller is the operation of an output metering valve.

16. The gas injection system of claim 13, further comprising a sensor capable of sensing a pressure within the vacuum chamber communicably connected to the controller, whereby the gas injection system may be controlled in response to the pressure.

17. The gas injection system of claim 13, further comprising:
   a sensor capable of sensing a composition of an atmosphere within the vacuum chamber; the sensor communicably connected to the controller, whereby the gas injection system may be controlled in response to the composition.

18. The gas injection system of claim 17, wherein the sensor is a residual gas analyzer.

19. The gas injection system of claim 17, wherein the sensor is an optical spectrometer.

20. The gas injection system of claim 1, further comprising:
   a recognition device for reading information about the cartridge; and an identification device attached to the cartridge and having coded information regarding one or more characteristics of the cartridge, the identification device communicably connected to the recognition device, such that the identification device supplies the coded information to the recognition device.

* * * * *